US006383771B1

(12) United States Patent
Birkmayer

(10) Patent No.: US 6,383,771 B1
(45) Date of Patent: May 7, 2002

(54) ENZYME-BASED ASSAY FOR DETERMINING EFFECTS OF EXOGENOUS AND ENDOGENOUS FACTORS ON CELLULAR ENERGY

(75) Inventor: Georg D. Birkmayer, Vienna (AT)

(73) Assignee: Birkmayer Pharmaceuticals, New York, NY (US)

( * ) Notice: Subject to any disclaimer, the term of this patent is extended or adjusted under 35 U.S.C. 154(b) by 76 days.

(21) Appl. No.: 09/631,692

(22) Filed: Aug. 3, 2000

Related U.S. Application Data

(62) Division of application No. 08/957,656, filed on Oct. 24, 1997, now Pat. No. 6,248,552.

(51) Int. Cl.[7] .................................................. C12Q 1/26
(52) U.S. Cl. ............................. 435/25; 435/7.4; 435/4
(58) Field of Search ................................ 435/25, 7.4, 4

(56) References Cited

U.S. PATENT DOCUMENTS 4,654,301 A     3/1987  Garth et al. ................... 435/26

FOREIGN PATENT DOCUMENTS

EP          0 504 865 A1    9/1992  ............ C12Q/1/30

OTHER PUBLICATIONS

Magnani, et al., Redox and Energetic State of Red Blood Cells in G6PD Deficiency, Heterozygous β–Thalassemia and the Combination of Both, Acta Haemat. (Basel), 1986, 75(4), 211–214.

Reichmann, et al., Respiratory Chain and Mitochondrial Deoxyribonucleic Acid in Blood Cells from Patients with Focal and Generalized Dystonia, Movement Disorders, 1994, 9(6), 597–600.

Mitzkat, et al., Enzyme Patterns of the Energy–Linked Metabolism in Blood Cells of Human Diabetics, Hormone and Metabolic Research, 1972, 4(2), 107–110.

Ramakrishna, et al., Influence of Cerebral Ischemia and Post–Ischemic Reperfusion on Mitochondrial Oxidative Phosphorylation, J. Bioenerg. Biomembr., 1990, 22(1), 61–80.

*Primary Examiner*—Jean C. Witz
(74) *Attorney, Agent, or Firm*—Kenyon & Kenyon

(57) ABSTRACT

Disclosed herein is a method for determining the effect of either endogenous and exogenous factors on the energy producing capacity of cells comprising the steps of obtaining a sample of whole blood from the test subject, in which sample there is present an endogenous source of an oxidoreductase enzyme participating, directly or indirectly, in cellular energy production; adding to a portion of that sample an effective amount of a substrate associated with the enzyme implicated in cellular energy production; and measurement of an analytical signal the level of which is proportional to the endogenous level of an endogenously present cofactor of the enzyme. Preferably, in the method of the invention, the test subject is a mammal. More preferably, the test subject is a human.

6 Claims, 3 Drawing Sheets

ENZYME-BASED ASSAY FOR DETERMINING EFFECTS OF EXOGENOUS AND ENDOGENOUS FACTORS ON CELLULAR ENERGY

CROSS REFERENCE TO RELATED APPLICATIONS

The present application is a divisional of application Ser. No. 08/957,656 filed Oct. 24, 1997, now U.S. Pat. No. 6,248,552, the subject matter of which is incorporated herein by reference.

FIELD OF THE INVENTION

This invention relates in general to methods to monitor the energy enhancing effect of the reduced form of species such as nicotinamide adenine dinucleotide (NADH), nicotinamide adenine dinucleotide phosphate (NADPH), Coenzyme Q10, reduced form of Coenzyme Q10, adenosine triphosphate (ATP) and physiologically acceptable salts thereof, through determination of the relative activity of the energy-producing enzyme NADH cytochrome C reductase in whole blood.

BACKGROUND OF THE INVENTION

Every living cell needs energy to survive. This energy is produced, according to a process known as oxidative phosphorylation, in form of the chemical entity adenosine triphosphate (ATP).

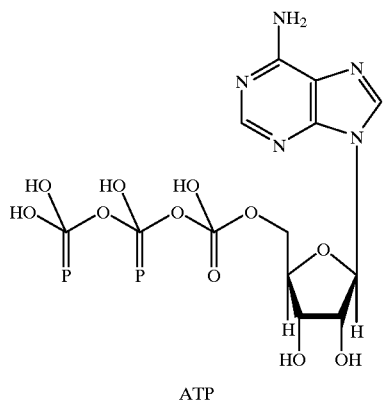

ATP

The key enzyme in the production of ATP is NADH cytochrome C reductase, also known as Complex I-III. This enzyme reduces cytochrome C by using the reducing agent NADH, the reduced form of nicotinamide adenine dinucleotide. The reduced cytochrome C is then oxidized by the enzyme cytochrome C oxidase (Complex IV) to form water. In other words, the reduced form of NADH, also called Coenzyme I, uses ubiquitous oxygen in the cell to form water and 3 ATP molecules in accordance with the following general reaction scheme:

$NADH+H^++\frac{1}{2}O_2+3P_i+3ADP \rightarrow NAD^++3ATP+4H_2O.$

Thus, with one NADH molecule, three ATP molecules are obtained having an energy of approximately 21 kilocalories. This process is set forth schematically in FIG. 1, where FeS is Reiske iron sulfur protein; ADP=adenosine diphosphate; and $b_{562}$, $b_{566}$, $c_1$, a and $a_3$ are cytochromes. The enzymes depicted in FIG. 1 are referred to as Complex I (NADH:ubiquinone oxidoreductase); Complex II (succinate dehydrogenase); Complex III (ubiquinone:cytochrome C oxidoreductase); Complex IV (cytochrome C oxidase); and Complex V (ATP synthase). These enzymes, whose energy-related functions occur in the mitochondria of the cell, are assembled from 13 polypeptides coded by the mitochondrial DNA (mtDNA) and approximately 50 polypeptides coded by the nuclear DNA (nDNA). This system of five complexes also constitutes what is referred to as the electron transport chain (ETC), the common pathway for cellular energy metabolism, through which enzyme-catalyzed redox processes achieve electron transfer among critical substrate species.

NADH cytochrome C reductase is the first and key enzyme of this energy producing process. The greater the activity of NADH cytochrome C reductase, the higher the cellular output of energy. Illustratively, the more energy a cell needs, the more NADH it contains. For example, heart cells have 90 $\mu$g/g tissue; brain and muscle cells contain 50 $\mu$g/g tissue; liver cells contain 40 $\mu$g/g; and red blood cells contain 3 $\mu$g/g tissue. Thus, the activity of NADH cytochrome C reductase, directly linked to the amount of NADH present in the cell, reflects the energy producing capacity of a cell. Alberts, B., Bray, D., Lewis, J., Raff, H., Roberts, K., and Watson, J. D., "Energy Conversion: Mitochondria and Chloroplasts," in *Molecular Biology of the Cell*, 3rd Ed., Garland Publishing Inc., pp. 653–720, 1994; Lehninger, A. L., "Vitamins and Coenzymes," in *Biochemistry*, 2nd Ed., The John Hopkins University School of Medicine, Worth Publishers, Inc., pp. 337–342, 1975.

It has been shown in a variety of diseases (the so-called mitochondrial diseases) that energy production, in particular the activity of NADH cytochrome C reductase (Complex I-III), is decreased. This has been demonstrated not only in brain and muscle tissue, but also in platelets. Cooper, J. M., Mann, V. N., Krige, D., and Schapira, A. H. V., "Human mitochondrial complex I dysfunction," *Biochemica et Biophysica Acta* 1101, 198–203 (1992); Mizuno, Y., et al., "Deficiencies in Complex I Subunits of the Respiratory Chain in Parkinson's Disease," *Biochemical and Biophysical Research Communication* 163, 1450–1455 (1989); Shoffner, J. M., Wafts, R. L., Juncos, J. L., Torroni, A., and Wallace, D. C., "Mitochondrial Oxidative Phosphorylation Defects in Parkinson's Disease," *Ann. Neurol.* 30, 332–339 (1991). This has been found both in patients with Parkinson's disease (PD) and in patients with Alzheimer's disease. A further demonstration of the link between cytochrome C reductase activity and disease conditions involves the Parkinson inducing toxin, 1-methyl-4-phenyl-1,2,3,6-tetrahydropyridine (MPTP), a compound that irreversibly inhibits and destroys NADH cytochrome C reductase in certain brain areas causing Parkinsonian-like symptoms. Benecke, R., Strumper, P., and Weiss, H., *Brain* 1993, Vol. 116, Part 6, pp. 1451–1463. These and other similar findings have significant implications for investigations into the etiology of conditions such as Alzheimer's and Parkinson's diseases.

Another known enzyme toxin is azidothymidine (AZT) which is used in the treatment of AIDS patients. This toxin damages NADH cytochrome C reductase, causing a reduction of energy production in the cell. Dalakas, M. C., IIIa, I., Pezeshkpour, G. H., Laukaftis, J. P., Cohen, B, and Griffin, J. L. "Mitochondrial myopathy caused by long-term zidovudine therapy," *New Engl. J.Med.* 322, 1098–1105 (1990). By measuring the activity of NADH cytochrome C reductase in muscle tissue biopsy, it was demonstrated that AZT destroys the enzyme's activity, consequently blocking the energy production of the cells leading to muscle atrophy.

In addition to substances known to have an inhibitory effect on the activity of key enzymes related to cellular processes for the production of energy, there are also substances, such as the reduced form of nicotinamide adenine dinucleotide (NADH) and nicotinamide adenine dinucleotide phosphate (NADPH), either endogenous or introduced exogenously, that are able to enhance NADH cytochrome C reductase activity and, consequently, cellular energy production. These two co-enzymes, and their pharmaceutically acceptable salts, have been shown to be useful in the treatment of Parkinson's Disease (PD). The effectiveness of these agents for this purpose is disclosed in U.S. Pat. Nos. 4,970,200, 5,019,516, and 5,332,727, the disclosures of which are incorporated herein by reference. In addition, these substances are effective in the treatment of Alzheimer's disease, as disclosed in U.S. Pat. No. 5,444,053, the disclosure of which is also incorporated herein by reference. These substances have also been demonstrated to be effective in supplying additional energy to healthy individuals as disclosed in EP 0 496 479 131.

Assay methods for the determination of NADH cytochrome C reductase activity have been described for many tissues, in particular muscle, liver, brain and heart cells. See, for example, Hatefi, Y. and Stiggall, D. L. (1978b), "Preparation and properties of NADH:cytochrome C oxidoreductase (Complex II)," in *Methods in Enzymology*, 53, Fleischer, S. and Packer, L., eds, pp 5–10, Academic Press, New York, 1978; Trounce, I., Byrne, E. and Marzuki, S., "Decline in skeletal muscle mitochondrial respiratory chain function: Possible factors in ageing," *Lancet* 1989, 637–639 (assay of muscle tissue); Yen, T.-C., et al., "Liver mitochondrial respiratory functions decline with age," *Biochem. Biophys. Res. Comm.* 165, 994–1003 (1989) (assay of liver tissue); Nakagawa-Hattori, Y., et al., "Is Parkinson's disease a mitochondrial disorder?" *J. Neurol. Sci.* 107, 29–33 (1992) assay of muscle tissue obtained post-mortem); Mizuno, Y., et al., "Effects of 1-methyl-1-phenyl-1,2,3,6-tetrahydropyridine and 1-methyl-4-phenylpyridinium ion activities of the enzymes in the electron transport system in mouse brain," *J. Neurochem.* 48, 1787–1793 (1987) (assay of mouse brain tissue); Reichman, H. et al., "Respiratory chain and mitochondrial deoxyribonucleic acid n blood cells from patients with focal and generalized dystonia," *Movement Disorders* 9, 597–600 (1994) (assays of platelet homogenate).

Indeed, cofactors in oxidative phosphorylation processes have seen widespread use in analytical procedures due to the extremely high molar absorptivities demonstrated by species such as NADH which exhibits a unique absorption maximum at approximately 340 nm, along with an even stronger maximum at about 270 nm that is shared with the oxidized form of the cofactor, $NAD^+$. By way of example, the concentration of alcohol in solution can be determined in an enzyme-based assay by adding an excess of $NAD^+$ and a suitable quantity of the $NAD^+$-dependent enzyme, alcohol dehydrogenase. The amount of NADH formed by the enzyme catalyzed reaction, which amount can be easily monitored spectrophotometrically, is stoichiometrically related to the amount of alcohol originally present in solution. The utility of such enzyme-based assays can be further extended through the use of coupled reaction schemes in which the analyte of interest does not directly participate in the enzyme-catalyzed process that gives rise to an analytical signal, but is indirectly linked to such process by a coupled reaction mechanism. However, it should be noted that, despite the use of a common enzyme cofactor in these analytical procedures, all such procedures share a common trait in that they are limited to monitoring processes that are not directly implicated in cellular energy production. As a consequence, such processes are dependent on the addition of both exogenous enzyme and cofactor, such as NADH, in order to generate an analytical signal.

For those demonstrated analytical procedures more directly related to cellular energy processes, a number of specific additional limitations exist. For example, all tissue-based assays require the sampling of tissue through biopsy or other even more invasive surgical procedures. In many cases, the tissue site selected for sampling is so critical physiologically that it can only be sampled post mortem. Assays based on isolation from platelets derived from a blood sample acquired through conventional venipuncture techniques offer advantages over methods that require biopsy of muscle or other tissue. However, such techniques suffer from the serious drawback that observed enzyme activity is dependent on the level of purification of the platelet preparation, introducing a potential source of significant analytical error. Furthermore, platelet separation/purification techniques are inherently complex and time consuming, adding significantly to the procedural overhead of enzyme-based methods from platelets. In addition, all of these enzyme-based assay methods can be further distinguished from the methods of the invention disclosed herein in that they all require the addition of exogenous sources of all cofactors involved in the enzymatic processes. Therefore, none of these methods can be characterized as assessing activity involving endogenous substrate.

In light of these and other significant drawbacks to the currently available assay methods for determination of energy-related enzyme activity, it is recognized that there is a need for an assay method that is simple in both sampling and procedure, as well as one that is efficient and well-suited to routine application. Toward that end, the inventor herein discloses an enzyme-based assay method that can be used with whole blood samples that has utility for assessment of the energy-producing capacity of test subjects, either before and/or after clinical treatments that include the ingestion of exogenous sources of NADH and related compounds.

SUMMARY OF THE INVENTION

In one aspect the present invention provides a method for the determination of the relative energy producing capacity of cells present in a sample of whole blood obtained from a test subject, wherein the method comprises the steps of obtaining a sample of whole blood from the test subject, in which sample there is present an endogenous source of an oxidoreductase enzyme participating, directly or indirectly, in cellular energy production; adding to a portion of that sample an effective amount of a substrate associated with the enzyme implicated in cellular energy production; and measurement of an analytical signal the level of which is proportional to the level of an endogenously present cofactor of the enzyme. Preferably, in the method of the invention, the test subject is a mammal. More preferably, the test subject is a human.

In another aspect, the method of the present invention involves an oxidoreductase enzyme selected from the group consisting of NADH:ubiquinone oxidoreductase, succinate dehydrogenase, ubiquinone:cyctochrome c oxidoreductase, cyctochrome C oxidase, ATP synthase, and combinations thereof. Alternatively, the method of the present invention involves an oxidoreductase enzyme selected from the group consisting of cytochrome C reductase (Complex I-III), dihydroubiquinone-cytochrome C oxidoreductase (coenzyme Q10), NADPH cytochrome B reductase, citrate synthetase, isocitrate dehydrogenase, alphaketoglutarate, succinate dehydrogenase, fumarase, and malate dehydrogenase and mixtures thereof.

In still another aspect, the method of the present invention involves an endogenously present cofactor selected from the group consisting of nicotinamide adenine dinucelotide ($NAD^+$), the reduced form of nicotinamide adenine dinucelotide (NADH), nicotinamide adenine dinucelotide phosphate ($NADP^+$), and the reduced form of nicotinamide adenine dinucelotide phosphate (NADPH).

In an alternative embodiment, the present invention contemplates a method for determination of the effect of endogenous factors on the cellular energy producing capability of cells present in a sample of whole blood obtained from a test subject, the method comprising testing a sample of whole blood obtained from the test subject according to a method comprising the steps of obtaining a sample of whole blood from the test subject, in which sample there is present an endogenous source of an oxidoreductase enzyme participating, directly or indirectly, in cellular energy production; adding to a portion of that sample an effective amount of a substrate associated with the enzyme implicated in cellular energy production; and measurement of an analytical signal the level of which is proportional to the endogenous level of an endogenously present cofactor of the enzyme.

In an another embodiment, the present invention provides a method for the determination of the effect of exogenous factors on the cellular energy producing capability of cells present in a sample of whole blood obtained from a test subject, the method comprising the steps of testing a sample of whole blood obtained from the test subject according to a method comprising the steps of obtaining a sample of whole blood from the test subject, in which sample there is present an endogenous source of an oxidoreductase enzyme participating, directly or indirectly, in cellular energy production; adding to a portion of that sample an effective amount of a substrate associated with the enzyme implicated in cellular energy production; and measurement of an analytical signal the level of which is proportional to the endogenous level of an endogenously present cofactor of the enzyme, the sample obtained prior to action of the exogenous factor on the test subject; testing a sample of whole blood obtained from the test subject according to a method comprising the steps of obtaining a sample of whole blood from the test subject, in which sample there is present an endogenous source of an oxidoreductase enzyme participating, directly or indirectly, in cellular energy production; adding to a portion of that sample an effective amount of a substrate associated with the enzyme implicated in cellular energy production; and measurement of an analytical signal the level of which is proportional to the endogenous level of an endogenously present cofactor of the enzyme, the sample obtained after action of the exogenous factor on the test subject; and comparing the results of the first measurement with the second measurement.

Specifically, the method of the present invention encompasses a method wherein the exogenous factor is exposure of the test subject to a substance capable of exerting a toxic effect on an oxidoreductase enzyme participating, directly or indirectly, in cellular energy production, or exposure of the test subject to a substance capable of enhancing the activity of an oxidoreductase enzyme participating, directly or indirectly, in cellular energy production.

In yet another alternative embodiment, the present invention provides a method for the determination of the relative energy producing capacity of cells present in a sample of whole blood obtained from a test subject comprising obtaining a sample of whole blood from the test subject, in which sample there is present an endogenous source of cytochrome C reductase; adding to a portion of that sample an effective amount of cytochrome C; measuring the absorbance of a mixture obtained from the previous two steps at 550 nm 60 seconds after mixing; measuring the absorbance at 550 nm of the mixture of step of the previous step after 300 sec; and calculating the moles of NADH present in the sample according to the following relationship:

$$\text{nmol } CytC_{red} = \frac{O.D._{550}(\text{at 60 sec}) - O.D._{550}(\text{at 300 sec})}{5} \cdot 13$$

$$= \text{nmol } NADH \text{ (endogenous)}$$

DETAILED DESCRIPTION OF THE PREFERRED EMBODIMENTS

Figure 1:
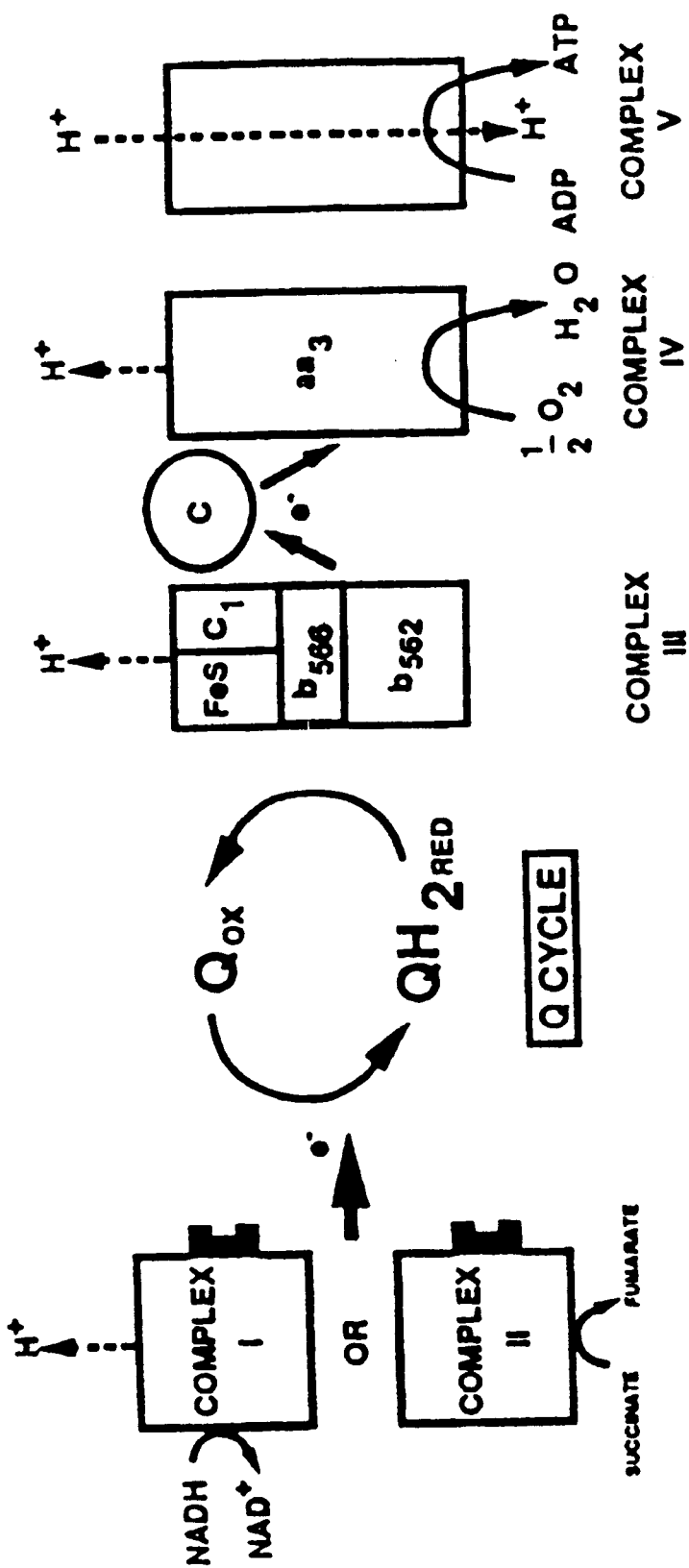
FIG. 1 is schematic representation of the redox processes occurring within the electron transport chain.

Concomitant with the discovery that electron transport chain (ETC) activity can be enhanced in both diseased and healthy individuals through ingestion of exogenous sources of ETC cofactors such as the reduced form of nicotinamide adenine dinucleotide, NADH, and the reduced form of nicotinamide adenine nucleotide phosphate, NADPH, there is the recognized need for an assay method to determine the effects of such treatment that is simple, reproducible, free from systematic errors and amenable to routine determinations. Toward this end, there is disclosed herein an enzyme-based assay method based upon an analysis of whole blood that satisfies the above criteria and that is capable of providing analytical data reflecting both endogenous cellular energy producing capability as well as changes in that capability due to either endogenous or exogenous factors. This method provides an alternative to those enzyme-based assay methods available in the prior art, wherein the alternative is considerably less complex and subject to far fewer potential interferences and, at the same time, capable of routine, relatively high volume use.

The importance of enzyme activity in the ETC is emphasized by studies illustrating a link between defects in or damage to any of the key proteins participating in this energy production cycle and recognized disease conditions. Disfunction of any one of the enzyme complexes involved in this reaction chain have been demonstrated to have a critical impact on the energy producing ability of the cell. From a molecular genetics viewpoint, this is understandable. Since the mitochondrial DNA (mtDNA) are tightly packed, with no non-coding intervening sequences, mutations in the mtDNA are highly likely to have direct functional implications. Continuous accumulation of mitochndrial mutations, such as have been postulated for ageing, are likely reflected in a deterioration in the cellular capacity for oxidative metabolism and may contribute to a decrease in overall functional capacity of the cell, both in skeletal muscle, and in other organs.

Parkinson's Disease and the Electron Transport Chain

There is accumulating evidence that the parthogenesis of Parkinson's disease may be related to both oxidative stress and a reduced ability to deal with oxidative stress. Endogenous factors include the metabolism of dopamine itself and conditions favoring oxidation in the substantia nigra. Several lines of evidence also strongly suggest that the basal glia are particularly susceptible to abnormalities of the mitochondrial ETC, as discussed above. A role for dysfunction of the ETC in PD was suggested by the discovery, mentioned above, that a metabolite of the neurotoxin 1-methyl-4-phenyl-1,2,3,6-tetrahydropyridine (MPTP), which causes a Parkinsonian syndrome, as discussed above, inhibits complex I in the ETC. Nicklas, W. J., Vyas, I., and Heikkila, R. E., "Inhibition of NADH-linked oxidation in brain mitochondria by 1-methyl-4-phenyl-pyridine, a metabolite of the neurotoxin, 1-methyl-4-phenyl-1,2,5,6-tetrahydropyridine," *Life Sciences*, 36, 2503–2508 (1985). After MPTP is metabolized to the active toxin $MPP^+$ by MAO-B in glia, $MPP^-$ is taken into dopaminergic neurons by the dopamine uptake pump, thus causing selective damage.

Decreased Complex I activity has been reported in both platelets of living PD patients Parker, W. D., Boyson, S. J., and Parks, J. K., "Abnormalities of the electron transport chain in idiopathic Parkinson's disease," *Ann. Neurol.* 26, 719–723 (1989), and postmortem brain of PD patients, Schapira, A. H. V., et al., "Anatomic and disease specificity of NADH CoQ10 reductase (complex I) deficiency in Parkinson's disease," *J. Neurochem.* 55, 2142–2145 (1990). Parker and colleagues found Complex I activity to be 45% of control levels in 10 of 10 patients, suggesting that the Complex I defect is present in an apparently unaffected tissue. By comparison, platelets have the advantage of not being subject to end-stage disease, neuronal dropout or postmortem artifact. Schapira and co-workers found Complex I activity to be 58% of control levels in postmortem substantia nigra, but not in a variety of other regions, including the caudate. They did not find any Complex I abnormality in the substantia nigra of Parkinsonian patients with multiple systems atrophy. Mizuno and colleagues, Mizuno, Y., et al., "Deficiencies in complex I subunits of the respiratory chain in Parkinson's disease," *Biochem. Biophys. Res. Commun.* 163, 1450–1455 (1989), found decreases in the amount of three subunits of Complex I by immunoblot in the striatum.

Alzheimer's Disease and other Dementia Conditions

There is general agreement on the pathology and biochemistry of Alzheimer's disease. Unfortunately, the pathology can be determined only after death by means of a brain autopsy. A brain autopsy of an Alzheimer's patient will show the presence of (1) cortical atrophy, (2) neuron loss, and (3) senile plaques and neurofibrillary tangles. A definitive diagnosis of Alzheimer disease is therefore possible only through histopathological examination of the brain tissue.

The major biochemical change identified in senile dementia of the Alzheimer's type (SDAT) is a deficiency of cholinergic neurotransmitter owing to the progressive loss of cholinergic presynaptic neurons located in the basal forebrain. There are gross similarities between the biochemical changes found in normal aging and in SDAT. However, there are also functional disturbances of the catecholaminergic system. It has been shown that catecholamine activity in the aged rat brain is reduced. The enzymatic activity of tyrosine hydroxylase (TH) as well as dopade-carboxylase (DOD) has been found significantly decreased in post-mortem samples of humans. Other post-mortem studies in humans have shown reduced levels of dopamine (DA) and noradrenaline (NA) related to age. These observations indicate that there is a decrease of the concentrations of catecholamine in the normal aged brain.

These findings provide evidence that the biochemical cause of cognitive dysfunction and dementia in SDAT is not only confined to the acetylcholinergic system, but also to the catecholaminergic system. This view is further supported by the clinical observation that in SDAT not only intellectual but also emotional and motor impairments are observed. In particular, motor impairments accompanied with other Parkinsonian-like symptoms are observed in 50 percent of Alzheimer patients. On the other hand, Parkinsonian patients frequently develop symptoms of dementia.

ETC defects have been observed in other neurodegenerative diseases. Parker and associates, Parker, W. D., et al., "Evidence for a defect in NADH:ubiquinone oxidoreductase (complex I) in Huntington's disease," *Neurology* 40, 1231–1233 (1990), reported finding a Complex I defect in 5 of 5 Huntington's disease patients, but no Complex I defect was found in 5 subjects at risk. A Complex IV defect was reported in 5 of 6 Alzheimer's patients. Parker, W. D., Filley, C. M., and Parks, J. K., "Cytochrome oxidase deficiency in Alzheimer's disease," *Neurology* 40, 1302–1303 (1990). Conversely, movement disorders are associated with toxin-induced or other genetic disturbances of the ETC. Poisoning with carbon monoxide and cyanide, both inhibitors of the ETC, produces sequelae including Parkinsonism. The basal ganglia in general are affected grossly or functionally in known ETC disorders such as Leigh's disease, MELAS (mitochondrial encephalopathy, lactic acidosis, and stroke-like episodes), the variant of Leber's disease associated with dystonia, and 9 of 85 patients with a variety of mitochondrial myopathies. Truong, et al., "Movement disorders in mitochondrial myopathies. A study of nine cases with two autopsy studies," *Movement Disorders* 5, 109–117 (1990). The puzzling variety of clinical phenotypes that has been associated with functional defects of each of the ETC complexes may be due partly to tissue-specific isozymes or control mechanisms, but has yet to be fully explained.

Notable in many of these other ETC disorder is the common occurrence of functional defects in several of the complexes to the ETC. These defects may be due to leakage of free radicals generated in the ETC, which would normally be tightly bound to the complexes. Liberation of these free radicals by a malfunctioning complex could lead to nonselective damage to nearby membranes, other components of the ETC, and mitochondrial DNA. Alternatively, the underlying defect could lie in one of the nuclear-encoded proteins that direct or coordinate mitochondrial function, thus causing simultaneous dysfunction of one or more complexes.

Given the implication of the observation that damage, either genetic or exogenous, to any of the series of enzyme complexes critical to the functionality of the ETC can effect cellular energy-producing capacity, there is a need to both clinically treat the energy deficiencies associated with such damage, as well as a need to be ale to assess both the level of damage and the level of change associated with clinical treatment of such conditions.

Energy Assays

Concomitant with the realization that clinical treatment with NADH can directly affect the cellular activity of cytochrome C reductase is the recognition that convenient, sensitive and accurate assays are required to facilitate assessment of the effects of various endogenous conditions, as well as active treatment regimens, on cellular energy production. As discussed above, the previously available assay methods are all characterized by significant deficiencies that render them less than ideal for routine, high volume assays of enzymatic activity in the ce!!. Disclosed herein is an enzymatic assay method for determining the amount of endogenous NADH from whole blood the results of which can be directly correlated to cellular energy production. This method offers significant advantages over tissue-based assay methods. Although determination of the tissue level of NADH can be done by extraction methods, analyzing the extract by high performance liquid chromatography (HPLC), such procedures are very elaborate, not very sensitive, and ill suited for use on a routine basis.

An enzyme that which can be measured in a similar way as NADH cytochrome C reductase is dihydroubiquinone-cytochrome C oxidoreductase (coenzyme Q10). Also, with this enzyme it is possible to determine an enzymatic activity without adding exogenous coenzyme Q10 because a sufficient amount of CoQ1 is present in the enzyme preparation (cell homogenate). Due to the recognized fact that the activity of this enzyme also declines with ageing, it is possible to show whether nutritional supplements containing coenzyme Q10 lead to an increase in endogenous CoQ10 concentration and, hence, to an increase in cellular energy production in the form of ATP. The stoichiometric relationship between ATP and coenzyme Q10 is 1:1.

Another enzyme capable of using the endogenous substrate concentration is NADPH cytochrome B reductase. It is likely that this enzyme is capable of functioning according to the principles observed with NADH cytochrome C reductase. Furthermore, it is reasonable to assume that all the enzymes involved in the citric acid cycle can be used for the same purpose of determining the endogenously present substrate. The first enzyme in this cycle is citrate synthetase. This enzyme uses oxalacetate and acetyl CoA to produce citrate. This enzyme may be used to determine the endogenous concentration of acetyl CoA. The next relevant enzyme is isocitrate dehydrogenase. This enzyme leads to the formation of oxalosuccinate and alphaketoglutarate. The next enzyme is alphaketoglutarate dehydrogenase complex, forming succinyl CoA which uses NAD+ (the oxidized form of NADH) as substrate. This enzyme would allow the determination of the endogenous NAD+ concentration in the cellular homogenate. The next enzyme in the citric acid cycle is succinate dehydrogenase which forms fumarate from succinate. This enzyme allows the determination of the endogenous substrate FAD (flavin adenine dinucleotide). Fumarate is then transformed into malate by the enzyme fumarase. The citric acid cycle is closed by the final reaction of the enzyme malate dehydrogenase which transforms malate into oxalacetate using NAD+ as substrate. This enzyme may also be used to determine the endogenous concentration of NAD+.

EXAMPLES

This invention will now be described in detail with respect to showing how certain specific representative embodiments thereof can be implemented, the materials, apparatus and process steps being understood as examples that are intended to be illustrative only. In particular, the invention is not intended to be limited to the methods, materials, conditions, process parameters, apparatus and the like specifically recited herein.

Example 1

Assay of Whole Blood for Cellular Energy Producing Capacity.

Enzyme Preparation A 1-mL portion of a whole blood sample obtained from a subject by venipuncture is preserved by addition of a suitable preserving agent such as that provided by a citrate solution. To a 100-$\mu$L sample of this citrate blood is added 900 $\mu$L of phosphate balanced salt solution (PBS) at pH =7.8. The resulting 1-mL portion of buffer-diluted citrate blood is sonified with an apparatus such as that available from BRANSON at a duty cycle of 40%, output position 3. Sonification is repeated a total of ten times for 10 seconds each. An additional 1-mL volume of PBS is added to the sonified solution. The PBS-diluted solution represents the enzyme preparation utilized for further assay.

Substrate preparation A 10-mg sample of cytochrome C, obtainable from conventional sources such as Sigma Chemical, St. Louis is dissolved in 9.6 mL of distilled water. To this is added add 200 $\mu$L of 0.1 M $NaN_3$ (sodium azide) and 200 $\mu$L of PBS (pH 7.8).

Performance of the enzyme assay A 900-$\mu$L volume of cytochrome C solution (reaction substrate) is pipetted into a 1-mL (PMMA) cuvette. The sample is mixed and allowed to incubate for 15 minutes at 37°. A 100-µL volume of enzyme preparation is added to the sample cuvette and mixed thoroughly. The absorption of reduced cytochrome C at 550 nm is measured exactly 60 seconds after addition of the enzyme preparation to the cuvette. The absorption of cytochrome C at 550 nm is again measured after 5 minutes of incubation at 37° C. after the first measurement. A reference cuvette containing 900 µL of cytochrome C solution (substrate) and 100 µL PBS (without enzyme solution) is used for the spectrophotometric measurement.

Determination of enzymatic activity The specific activity of the enzyme species is expressed as nanomoles (nmol) of cytochrome C reduced per µL blood per 5 minutes. For quantitative analyses, a calibration curve with 0, 30, 50, 100, 130 nmol reduced cytochrome C concentrations is prepared. For calculation of the enzymatic activity expressed per blood cell, the number of red blood cells, white blood cells and IS platelets are determined. The cell counts of these cells can be determined from the undiluted citrate blood according to standard procedures.

Calculation of enzymatic activity The quantity of cytochrome C reduced can be calculated according to the following expression which, in turn, provides the amount of endogenous NADH available, where O.D.=optical density:

$$\text{nmol } CytC_{red} = \frac{O.D._{550}(\text{at } 60 \text{ sec}) - O.D._{550}(\text{at } 300 \text{ sec})}{5} \cdot 13$$

$$= \text{nmol } NADH \text{ (endogenous)}$$

Example 2

Correlation Between Aging and Cellular Energy Producing Capacity.

Figure 2A:
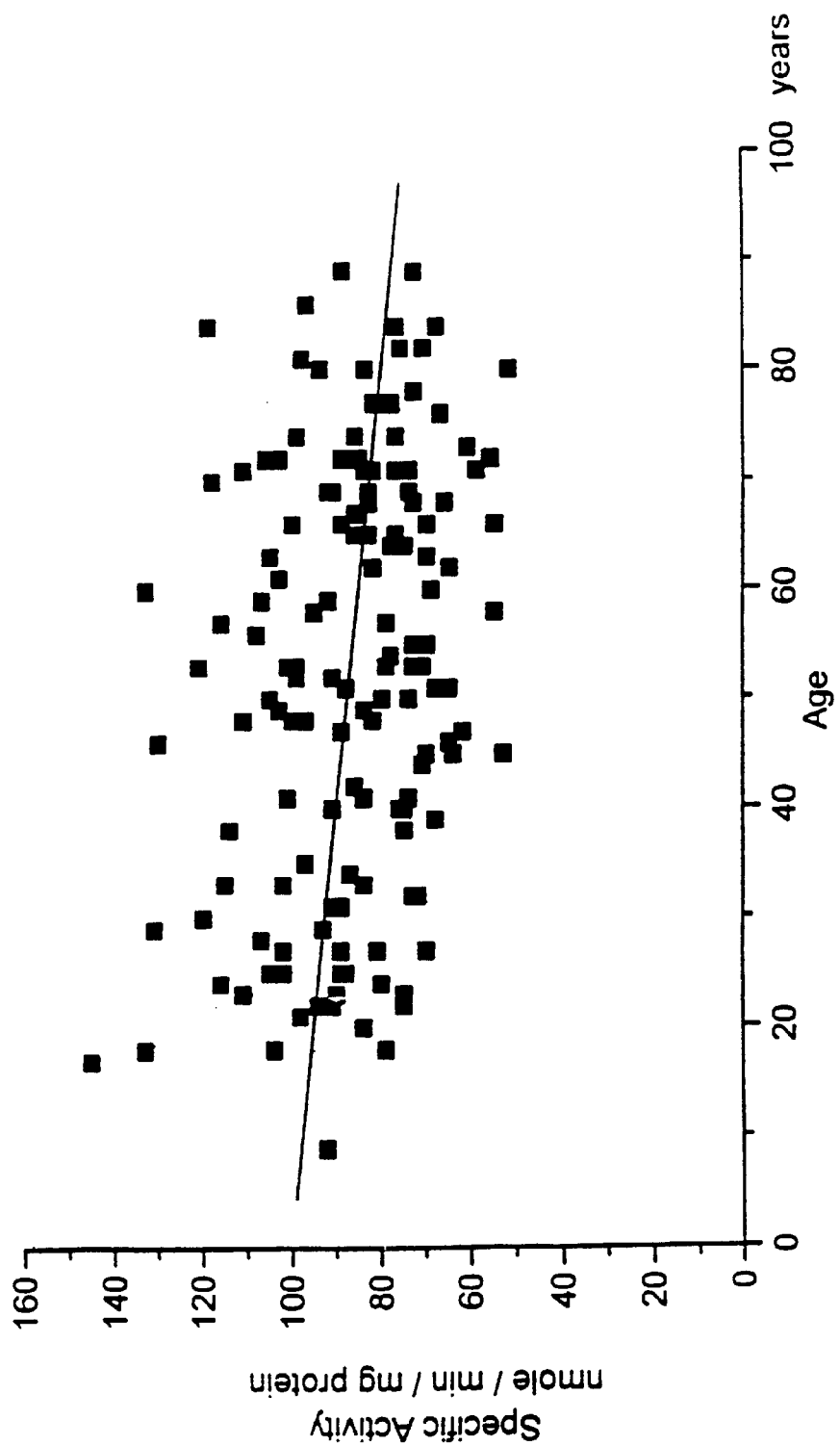
FIG. 2 is a plot, presented in two panels, 2A and 2B, of the results of data obtained through the method of the present invention illustrating the decline in endogenous cellular energy production with increasing age.
Figure 2:
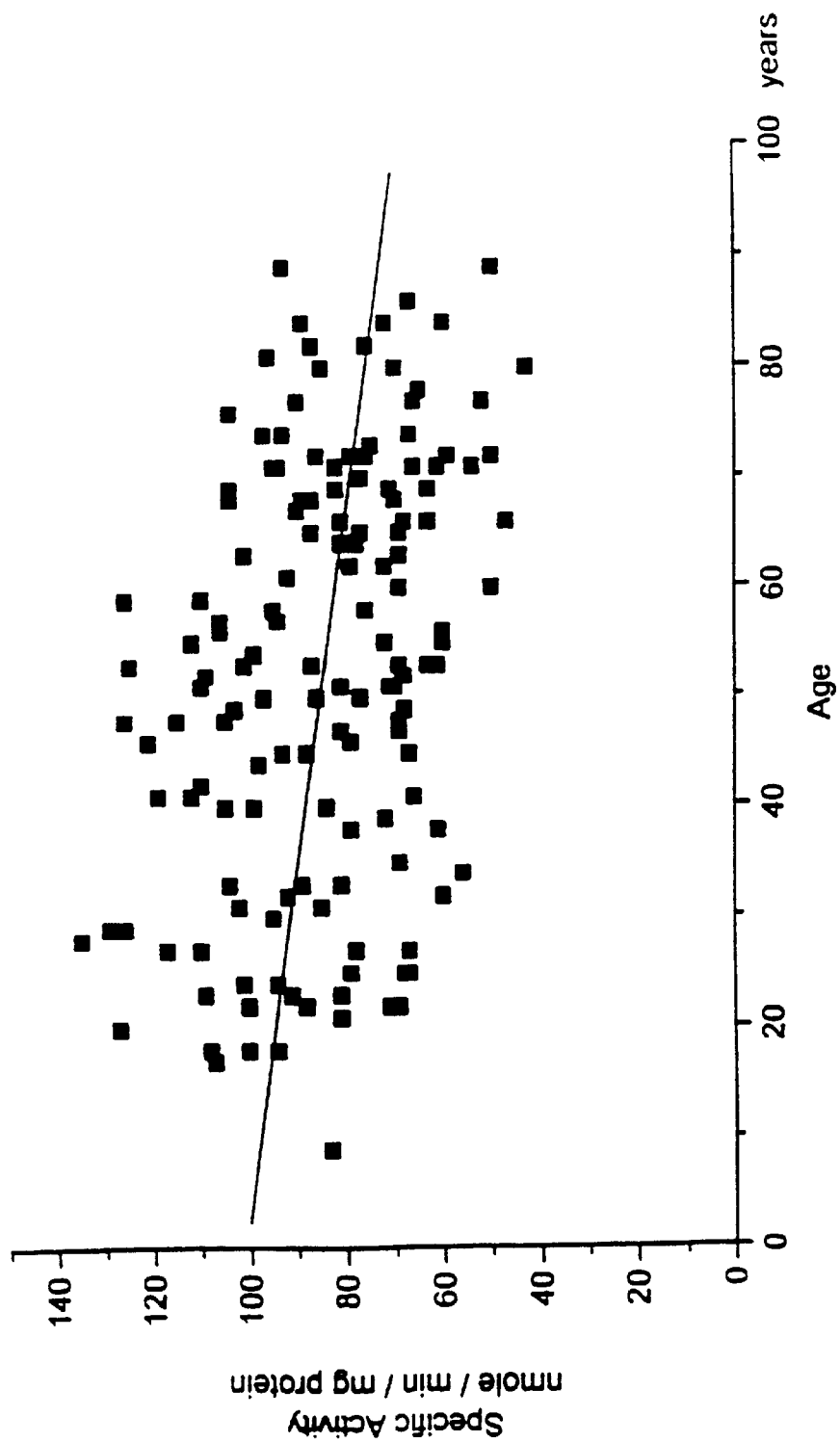

Blood from patients of various ages was tested according to the assay method of the present invention. The results of these analyses indicated that there is a decline in the intracellular NADH content with age. In other words, younger people have higher NADH levels and, hence, a greater energy production than older people. Although these results are consistent with intuitive expectations, this series of analyses represented the first documented data from an enzyme assay to support such a conclusion. The data from these analyses is presented graphically in panels 2A and 2B of FIG. 2.

Example 3

Assessment of Impact on Energy Producing Capability of Competitive Cyclists Through Intake of Exogenous NADH Twenty international caliber athletes (triathletes or cyclists) were selected for an open label trial. The age of the athletes was 18 to 35 years with a mean value of 24.2 years. Eligible athletes received a physical examination including electrocardiogram (ECG), as well as a number of laboratory tests including hematology, blood sedimentation rate, GOT, GPT, GGT, bilirubin, BUN, creatinine, uric acid, sodium, potassium, chloride, magnesium, iron, glucose, cholesterol (HDL and LDL), triglyceride, creatine kinase (MB isoenzyme) and urine status. The examination also included a short medical history. Athletes were selected for the study after all examination parameter were found to be in the normal range.

Competitive cyclists received one 5-mg tablet daily of a stable oral dosage form of NADH for a period of one month. NADH cytochrome C reductase assays according to the general procedure of Example 1 were performed on each subject before and after the treatment period. Results of these assays are presented below in Table 1. In nineteen of the twenty athletes, an increase in the endogenous NADH cytochrome C reductase activity was found. This increase indicates that NADH ingested orally led to an increase in intracellular NADH content and, hence, in energy production.

The performance quality, reaction speed and constancy of attention also was tested in these athletes. The performance quality was assessed by the accuracy with which a task was done, i.e., generally in terms of the number of correct identifications of stimuli. Methods used for determination of performance quality were measurement of the continuous attention, vigilance, and the cognitrone program of the Vienna Test system (Dr. Schuhfried Ges.m.b.H., Austria). For examination of the physical performance, a bicycle ergometer (Oxycon-Alpha, Jager Inc., Vienna, Austria) was used. These tests were performed twice: first, one day before starting with NADH; second, 4 weeks later. One tablet containing 5 mg NADH was taken by the athletes daily before breakfast on an empty stomach for 4 weeks. The volume and the intensity of the training and exercise program of the athletes was kept constant over that period. The physical and mental performance of these athletes was found to be improved in those nineteen who exhibited an increased NADH cytochromic reductase activity. Data reflecting this is presented below in Tables 2–4.

TABLE 1

Changes in NADH activity for competitive cyclists

| Subject No. | Enzyme Activity before NADH intake | Enzyme Activity after NADH intake | % Difference |
|---|---|---|---|
| 1 | 1.3 | 2.1 | 61.50% |
| 2 | 1.5 | 2.3 | 53.30% |
| 3 | 1.2 | 1.9 | 58.30% |
| 4 | 1.7 | 2.4 | 41.20% |
| 5 | 1.4 | 2.1 | 50.00% |
| 6 | 1.4 | 2.2 | 57.10% |
| 7 | 1.5 | 2.2 | 46.70% |
| 8 | 1.3 | 2.3 | 76.90% |
| 9 | 1.6 | 2.4 | 50.00% |
| 10 | 1.7 | 2.5 | 47.10% |
| 11 | 1.5 | 2.2 | 46.70% |
| 12 | 1.4 | 2.3 | 64.30% |
| 13 | 1.6 | 2.4 | 50.00% |
| 14 | 1.5 | 2.4 | 60.00% |
| 15 | 1.7 | 2.5 | 47.10% |
| 16 | 1.8 | 2.7 | 50.00% |
| 17 | 1.7 | 2.5 | 47.10% |

TABLE 2

Summary of the results of the Dispersion of Reaction Times (DRT) measurements prior to and 4 weeks after intake of one 5-mg tablet NADH per day.

| | before NADH | after NADH | % alteration per person | SD (n = 17) | absolute alteration per person |
|---|---|---|---|---|---|
| Continuous attention | | | | | |
| correct reactions | 117.20 | 118.80 | 1.42 | 2.89 | |
| incorrect reactions | 2.71 | 1.59 | | | -1.12  2.00 |
| missed reactions | 2.65 | 1.24 | | | -1.41  3.22 |
| DRT (mean value) | 0.87 | 0.81 | -6.48 | 12.48 | |
| Dispersion | 0.19 | 0.17 | -11.59 | 23.89 | |
| Cognitrone | | | | | |
| Correct reactions | 185.20 | 190.10 | 2.98 | 6.54 | |
| DRT (mean) | 2.58 | 2.09 | -16.05 | 16.94 | |
| working time (min) | | | -14.36 | 16.18 | |
| Vigilance | | | | | |
| correct reactions | 97.94 | 97.88 | 0.01 | 3.28 | |
| incorrect reactions | 1.88 | 1.24 | | | -0.65  2.78 |
| missed reactions | | | | | 0.24  3.09 |
| DRT (mean) | 0.51 | 0.55 | 7.79 | 19.91 | |
| Dispersion | 0.10 | 0.11 | 4.79 | 31.85 | |

TABLE 3

Summary of the performance parameters as measured by spiro-ergometry before and 4 weeks after intake of 1 tablet NADH (5 mg) per day.

| | before NADH | | | | | |
|---|---|---|---|---|---|---|
| Parameters | mean | SD | min. | max. | med. | mean |
| $W_{max}$ | 331.00 | 32.90 | 277.00 | 404.00 | 335.00 | 340.00 |
| $W_{max}/kg$ | 4.70 | 0.40 | 4.10 | 5.60 | 4.60 | 4.90 |
| $Hf_{max}$ | 179.00 | 11.80 | 150.00 | 197.00 | 180.00 | 180.00 |
| $V_{max}$ | 150.00 | 20.40 | 106.00 | 177.00 | 148.00 | 163.00 |
| $VO_{2Max}$ | 4.72 | 0.47 | 4.06 | 5.79 | 4.77 | 4.98 |
| $VO_{2Max}/kg$ | 68.50 | 5.90 | 59.70 | 87.70 | 67.00 | 71.20 |
| $R_{max}$ | 1.00 | 0.10 | 0.90 | 1.10 | 1.00 | 1.00 |

| | after NADH | | | |
|---|---|---|---|---|
| $W_{max}$ | SD | min. | max. | med. |
| $W_{max}/kg$ | 43.90 | 277.0 | 433.00 | 339.00 |
| $Hf_{max}$ | .60 | 4.10 | 6.00 | 4.60 |
| $V_{max}$ | 12.50 | 150.0 | 192.00 | 182.00 |
| $VO_{2Max}$ | 23.70 | 137.0 | 218.00 | 155.00 |
| $VO_{2Max}/kg$ | 0.61 | 3.95 | 5.91 | 4.96 |
| $R_{max}$ | 8.20 | 61.1 | 88.20 | 68.70 |

$W_{max}$ = maximum performance

TABLE 4

Summary of lactate blood levels after maximum performance prior to and after 4 weeks of one 5-mg tablet NADH per day (n = 17).

| | before NADH | | after NADH | | Differences in percent | | | |
|---|---|---|---|---|---|---|---|---|
| Lactate Level | mean | SD | mean | SD | $D_{mean}$ | $D_{min}$ | $D_{max}$ | $D_{med}$ |
| 1 min. after maximum | 8.1 | 3.5 | 9.0 | 3.2 | 10.0 | -7.3 | 22.2 | 9.6 |
| performance 3 min. after maximum performance | 6.1 | 2.8 | 7.4 | 2.3 | 17.2 | -22.5 | 70.3 | -3.7 |

Example 4

Assessment of Impact on Energy Producing Capability of Soccer Players Through Intake of Exogenous NADH A study similar to that of Example 3 was performed with a European soccer team. Fifteen athletes received one 5-mg tablet daily of a stable oral dosage form of NADH for a period of one month. NADH cytochrome C reductase assays according to the general procedure of Example 1 were performed on each subject before and after the treatment period. Results of these assays are presented below in Table 5. The endogenous NADH cytochrome C reductase activity was found to increase indicating an increase in intracellular NADH level which corresponds to an increased energy production. This increased energy production was confirmed by improved physical performance on the treadmill or bicycle ergometer.

TABLE 5

Changes in NADH activity for soccer players

| Subject No. | Enzyme Activity before NADH intake | Enzyme Activity after NADH intake | % Difference |
|---|---|---|---|
| 1 | 0.8 | 2.1 | 162% |
| 2 | 1.2 | 2.1 | 75% |
| 3 | 1.5 | 1.6 | 6.60% |
| 4 | 1.4 | 1.5 | 7.10% |
| 5 | 1.0 | 1.2 | 20.00% |
| 6 | 1.2 | 1.3 | 8.30% |
| 7 | 1.4 | 1.6 | 20.00% |
| 8 | 1.4 | 1.6 | 20.00% |
| 9 | 1.4 | 1.3 | -8.30% |
| 10 | 1.4 | 1.4 | 0.00% |
| 11 | 1.2 | 1.6 | 33.00% |
| 12 | 1.1 | 1.1 | 0.00% |
| 13 | 1.4 | 1.6 | 20.00% |
| 14 | 1.2 | 1.4 | 16.00% |
| 15 | 1.4 | 1.5 | 7.10% |

Example 5

In an animal study, rats received one 2.5-mg tablet of NADH daily for three months. NADH cytochrome C reductase assays according to the general procedure of Example 1 were performed before and after a regimen of ingestion of exogenous NADH. An increase in the enzymatic activity was observed in all test animals indicating that orally ingested NADH leads to an increase of intracellular NADH concentration and, due to this, to an increased energy production. data are presented below in Table 6.

TABLE 6

Change in NADH activity in rats

| Subject No. | Enzyme Activity before NADH intake | Enzyme Activity after NADH intake | % Difference |
|---|---|---|---|
| 1 | 0.35 | 0.42 | 20.0% |
| 2 | 0.41 | 0.45 | 9.6% |
| 3 | 0.36 | 0.41 | 13.8% |
| 4 | 0.40 | 0.45 | 12.5% |
| 5 | 0.35 | 0.41 | 17.1% |
| 6 | 0.37 | 0.42 | 13.5% |
| 7 | 0.35 | 0.39 | 11.4% |
| 8 | 0.40 | 0.43 | 7.5% |
| 9 | 0.36 | 0.41 | 13.8% |
| 10 | 0.37 | 0.43 | 13.5% |

Those of skill in the art may recognize certain modifications to the various embodiments of the invention, which modifications are meant to be covered by the spirit and scope of the below-appended claims.

I claim:

1. A method for determination of effect of endogenous factors on the cellular energy producing capability of cells present in sample of whole blood obtained from a test subject, wherein the method comprises a) obtaining a sample of whole blood from the test subject said whole blood containing an endogenous oxidoreductase enzyme that participates, directly or indirectly, in cellular energy production and a co-factor for said oxidoreductase enzyme;

b) adding to a portion of said sample a reaction substrate for the oxidoreductase enzyme;

c) measuring amount of said substrate reduced by the oxidoreductase enzyme; and d) correlating the amount of substrate reduced with the energy producing capacity of the cells in said sample.

2. A method for determination of an effect of exogenous factors on the cellular energy producing capability in cells present in a sample of whole blood obtained from a test subject, wherein the method comprises a) administering the exogenous factor to the test subject;

b) obtaining a first sample of whole blood from the test subject prior to action of the exogenous factor on the test subject, said whole blood containing an endogenous oxidoreductase enzyme that participates, directly or indirectly, in cellular energy production and a co-factor for said oxidoreductase enzyme;

c) adding to a portion of said sample a reaction substrate for the oxidoreductase enzyme;

d) measuring amount of said substrate reduced by the oxidoreductase enzyme;

e) obtaining a second sample of whole blood from the subject after the exogenous factor acts on the test subject, and carrying out steps (c) and (d) with said second sample; and f) comparing the results obtained from the first sample with those of the second sample and correlating any difference between the first and second samples with the energy producing capacity of the cells in said samples.

3. The method of claim 2, wherein the exogenous factor is exposure of the test subject to a substance capable of exerting a toxic effect on an oxidoreductase enzyme participating, directly or indirectly, in cellular energy production.

4. The method of claim 2, wherein the exogenous factor is exposure of the test subject to a substance capable of enhancing the activity of an oxidoreductase enzyme participating, directly or indirectly, in cellular energy production.

5. A method for the determination of a relative energy producing capacity of cells present in a sample of whole blood obtained from a test subject, wherein the method comprises the following steps:

a) obtaining a sample of whole blood from the test subject, in which sample there is present an endogenous source of cytochrome C reductase;

b) adding to a portion of that sample an effective amount of cytochrome C;

c) measuring the absorbance of a mixture obtained by from steps a) and c) at 550 nm 60 seconds after mixing;

d) measuring the absorbance at 550 nm of the mixture of step d) after 300 sec; and e) calculating the moles of NADH present in the sample according to the following relationship:

$$\text{nmol } CytC_{red} = \frac{O.D._{550}(\text{at } 60 \text{ sec}) - O.D._{550}(\text{at } 300 \text{ sec})}{5} \cdot 13$$
$$= \text{nmol } NADH \text{ (endogenous)}.$$

6. A method for the determination of an effect of exogenous factors on the cellular energy producing capability of cells present in a sample of whole blood obtained from a test subject, the method comprising the steps of:

a) testing a sample of whole blood obtained from the test subject according to the method of claim 5, the sample obtained prior to action of the exogenous factor on the test subject;

b) testing a sample of whole blood obtained from the test subject according to the method of claim 5, the sample obtained after action of the exogenous factor on the test subject; and c) comparing the results of step a) with step b).

* * * * *

UNITED STATES PATENT AND TRADEMARK OFFICE
CERTIFICATE OF CORRECTION

PATENT NO. : 6,383,771 B1
DATED : May 7, 2002
INVENTOR(S) : G. Birkmayer

It is certified that error appears in the above-identified patent and that said Letters Patent is hereby corrected as shown below:

Title page,
Item [57], ABSTRACT,
Line 2, change from "either endogenoius and exogenous", change to -- either endogenous or exogenous --;

Column 5,
Line 13, change from "cytochrome c oxidoreductase", change to -- cytochrome C oxidoreductase --;
Lines 26, 27, 28 and 30, change from "dinucelotide", change to -- dinucleotide --;
Line 49, change from "an another" change to -- another --;

Column 7,
Line 24, change from "mitochndrial" change to -- mitochondrial --;

Column 9,
Line 11, change from "disorder" change to -- disorders --;
Line 29, change from "ale" change to -- able --;
Line 43, change from "ce!!" change to -- cell --;
Line 47, change from "offers.significant" change to -- offers significant --;
Line 59, change from "CoQ1" change to -- CoQ10 --;

Column 10,
Lines 10 and 27, change from "oxalacetate" change to -- oxaloacetate --;

Column 13,
Line 24, change from "0.01" change to -- -0.01 --;

Column 14,
Line 67, change from "production. data" change to -- production. Data --;

Column 15,
Line 15, change from "13.5%" change to -- 16.2% --;

UNITED STATES PATENT AND TRADEMARK OFFICE
CERTIFICATE OF CORRECTION

PATENT NO.   : 6,383,771 B1
DATED        : May 7, 2002
INVENTOR(S)  : G. Birkmayer It is certified that error appears in the above-identified patent and that said Letters Patent is hereby corrected as shown below:

Column 16,
Line 31, change from "obtained by from steps a) and c)" change to -- obtained from steps a) and b) --.

Signed and Sealed this

Twenty-fifth Day of March, 2003

JAMES E. ROGAN
*Director of the United States Patent and Trademark Office*